United States Patent [19]

Humphreys

[11] Patent Number: 4,604,295
[45] Date of Patent: Aug. 5, 1986

[54] VISIBLE LIGHT ABSORBING PEROXY-ESTERS

[75] Inventor: Robert W. R. Humphreys, Bergenfield, N.J.

[73] Assignee: Loctite Corporation, Newington, Conn.

[21] Appl. No.: 564,150

[22] Filed: Dec. 22, 1983

[51] Int. Cl.$^4$ .............................................. B05D 3/06
[52] U.S. Cl. .................................. 427/54.1; 560/302; 522/60; 522/181
[58] Field of Search ............ 204/159.23; 260/453 RZ; 427/54.1

[56] References Cited

U.S. PATENT DOCUMENTS

| | | | |
|---|---|---|---|
| 2,698,863 | 1/1955 | Dickey | 260/453 RZ |
| 3,637,798 | 1/1972 | Sulzberg et al. | 260/465 |
| 3,864,126 | 2/1975 | Nishide et al. | 96/1.5 |
| 3,987,088 | 10/1976 | Hodson et al. | 260/475 FR |
| 4,013,623 | 3/1977 | Turner et al. | 260/63 UY |
| 4,050,934 | 9/1977 | Turner | 96/1 R |
| 4,071,424 | 1/1978 | Dart et al. | 204/159.15 |
| 4,110,184 | 8/1978 | Dart et al. | 204/159.23 |
| 4,131,529 | 12/1978 | Osterlob et al. | 204/159.14 |
| 4,222,835 | 9/1980 | Dixon | 204/159.23 |
| 4,315,998 | 2/1982 | Neckers et al. | 204/159.15 |
| 4,351,853 | 9/1982 | Jochum et al. | 427/2 |
| 4,416,826 | 11/1983 | Neckers | 260/453 RZ |
| 4,457,818 | 7/1984 | Denyer et al. | 204/159.19 |
| 4,459,193 | 7/1984 | Ratcliffe et al. | 204/159.23 |

OTHER PUBLICATIONS

Abu-Abdoun et al, *Macromolecules*, 1984, 17, 282–288.

Leffler et al, *J. Am. Chem. Soc.*, vol. 93, No. 25, 1971, pp. 7005–7012.
L. Thijs, et al., *J. Org. Chem.* 44, 4123 (1979).
S. Gupta, et al., *J. Polymer Sci.*, 19 103–114 (1981).
T. Sulzberg et al., *J. Org. Chem.* 35, 2762–2769 (1970).
F. Moore et al., *JACS*, 49 1324, 1330 (1927).

*Primary Examiner*—John H. Newsome
*Attorney, Agent, or Firm*—Walter J. Steinkraus; Eugene F. Miller

[57] ABSTRACT

Compounds represented by the formula:

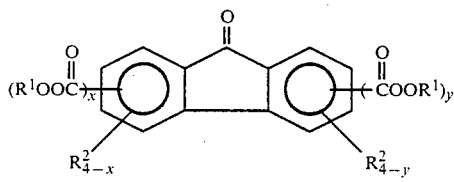

wherein
 $R^1$ is alkyl, aralkyl, alkoxyalkyl, alkenyl, alkynyl, carboxyalkyl or carboxyaryl;
 $R^2$ is any group which does not cause spontaneous decomposition of the peroxy group; and
 x and y are integers between 0 and 4 with x+y great than or equal to 1, are disclosed.

The inventive compounds are useful as visible and UV photoinitiators and as thermal or chemical initiators for curing compositions of ethylenically unsaturated monomers and prepolymers.

24 Claims, No Drawings

VISIBLE LIGHT ABSORBING PEROXY-ESTERS

BACKGROUND OF THE INVENTION

Photoinitiated curing of olefinically unsaturated compositions has a broad spectrum of industrial uses including polymer synthesis, elastomer vulcanization and the curing of adhesives, coatings and films. Typically the photoinitiators in such systems have primary activity in the ultraviolet (UV) region, with little or no visible light sensitivity. While this is often a useful property, e.g., when the composition needs to be stored or preapplied under conditions subject to visible light exposure, there are many applications in which it is desirable that a composition be cureable by exposure to visible light. For instance, in adhesive applications when bonding polymers which are transparent to visible light but not to UV light, effective visible light photoinitiators are particularly desirable. Polycarbonates are examples of such visible light transparent, UV light opaque polymers.

In other applications visible light initiated curable compositions are desirable because visible light is much cheaper and safer to produce than UV and requires less specialized equipment.

L. Thijs, S. Gupta, and D. Neckers, *J. Org. Chem.*, 44 4123 (1979), describe the synthesis and use of t-butyl peresters having an associated benzophenone chromophore as photoinitiators. These authors suggest that the photodecomposition characteristics of these perester compounds can be altered by the absorption characteristics of the associated chromophore. The same authors published subsequent papers, *J. Polymer Sci.*, 19, 103–114 and 855–868 (1981), in which the photoinitiating characteristics of other benzophenone peresters are examined.

SUMMARY OF THE INVENTION

The present invention relates to a novel class of peroxy ester or diacyl peroxide compounds which will efficiently generate free radicals capable of initiating polymerization of unsaturated olefins upon exposure to UV or visible light. The compounds are derivatives of 9-fluorenone which include at least one peroxy ester or diacyl peroxide group attached thereto. The compounds may be generally represented by formula (1):

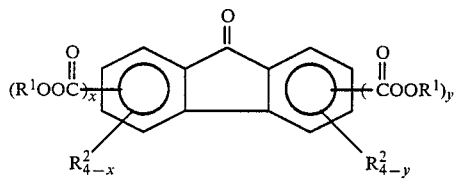

where
$R^1$ is alkyl, aralkyl, alkoxyalkyl, alkenyl, alkynyl, carboxyalkyl or carboxyaryl;
$R^2$ is any group which does not cause spontaneous decomposition of the peroxy group; and
x and y are integers between 0 and 4 with x+y greater than or equal to 1.

The various $R^1$ and $R^2$ groups many be the same or different. Preferably $R^2$ is selected from H, alkyl, alkoxy, carboalkoxy, silyl, organosiloxy, nitro, alkenyl, alkynyl, halo, or, when $R^1$ is not carboxyalkyl or carboxyaryl, amino, alkylamino or dialkylamino.

The inventive fluorenone peroxy esters will typically be monomeric molecules but may also be advantageous to utilize as polyphotoinitiators by linking the peroxy ester to a polymeric backbone through an appropriate $R^1$ or $R^2$ group.

The invention also encompasses a method of curing olefinically unsaturated compounds by exposing same to visible or UV light in the presence of a compound of the invention. Compositions of the inventive photoinitiators with olefinically unsaturated monomers are also within the scope of the instant invention.

The inventive peresters and diacyl peroxides will also undergo typical peroxide decomposition reactions, forming free radicals under heat or chemical activation. Accordingly, the inventive compounds may be used as a single initiator of a multiple cure system. For instance, coating compositions may be formulated employing the inventive compounds in which the surface is cured rapidly by exposure to UV or visible light with shadow areas curing by a slower chemically or heat activated mechanism.

DETAILED DESCRIPTION OF THE INVENTION

The inventive peroxy esters may be prepared from acid chlorides of the appropriate fluorenone carboxylic acid and an $R^1$ peroxy compound. The fluorenone carboxylic chlorides are prepared by conventional synthetic methods from the acid, using thionyl chloride, phosphorus pentachloride or other conventional reagents.

Fluorenone carboxylic acids are known. Examples include:
(a) fluorenone-1-carboxylic acid
(b) fluorenone-2-carboxylic acid
(c) fluorenone-4-carboxylic acid
(d) fluorenone-2,5-dicarboxylic acid
(e) fluorenone-2,7-dicarboxylic acid
(f) fluorenone-2,6-dicarboxylic acid
(g) 7-nitrofluorenone-2-carboxylic acid
(h) 7-methoxyfluorenone-2-carboxylic acid
(i) 7-acetylfluorenone-2-carboxylic acid
(j) 7-chlorofluorenone-2-carboxylic acid
(k) 7-bromofluorenone-2-carboxylic acid
(l) 7-cyanofluorenone-2-carboxylic acid
(m) 7-ethylfluorenone-2-carboxylic acid
(n) 7-butylfluorenone-2-carboxylic acid
(o) 7-butoxycarbonylfluorenone-2-carboxylic acid
(p) 7-propoxycarbonylfluorenone-2-carboxylic acid
(q) N,N-dialkyl-7-aminofluorenone-2-carboxylic acid
(r) 4,5,7-trinitrofluorenone-2-carboxylic acid
(s) 4,5-dinitrofluorenone-2,7-dicarboxylic acid
(t) 2,5,7-trinitrofluorenone-4-carboxylic acid.

Synthesis methods for the aforementioned fluorenone carboxylic acids may be found in the following references, the appropriate disclosures of which are incorporated herein by reference. Compound a: J. Am. Chem. Soc., 57, 2174(1935). Compounds b and d-q: U.S. Pat. No. 3,987,088. Compound c: Fieser and Fieser, "Advanced Organic Chemistry," Rheinhold Publishing Corporation, p. 807(1961). Compound r: U.S. Pat. Nos. 3,637,798 and 4,050,934. Compounds s and t: U.S. Pat. No. 3,637,798. A variety of additional mono- or polychloro, nitro, bromo, cyano, benzoyl and fluoro substituted fluorenone carboxylic acids are also reported in U.S. Pat. No. 3,864,126 as precursors to corresponding fluorenone carboxylic acid esters.

Synthesis of the inventive peroxy esters or diacyl peroxides may be exemplified by the following Examples 1–5.

EXAMPLE 1

9-Fluorenone-4-carbonylchloride was obtained by reacting 4.48 g 9-fluorenone-4-carboxylic acid and 12 ml (19.6 g) of $SOCl_2$ for three hours at reflux in a flask equipped with condensor, stirring bar and drying tube. Most of the excess $SOCl_2$ was removed by distillation (9 ml) and the remaining reaction product diluted with about 20–25 ml benzene. Hexane was then added until the solution became turbid, and the mixture refrigerated overnight. The resulting crystalline precipitate was collected by vacuum filtration, washed with hexane and dried in a vacuum desicator to yield 4.1 g of deep yellow crystals.

In a 125 ml erlenmeyer flask were placed 30 ml benzene and 1.23 g potassium t-butoxide. 1.10 g t-butyl hydroperoxide was added with stirring, producing a thick pasty mass. After 30 min., a solution of 2.43 g 9-fluorenone-4-carbonylchloride in 30 ml methylene dichloride was added in two equal portions and the mixture stirred in the dark for about an hour. The reaction mixture was then filtered, the filtrate placed on a rotary evaporator, and the solvents removed at temperatures of 35° C. or less. The product, containing the desired t-butyl perester of 9-fluorenone-4-carboxylic acid (4FP), was an orange oil.

EXAMPLE 2

The t-butyl peroxy ester of fluorenone-2-carboxylic acid (2FP) was prepared from the acid by the method of Example 1. The product was a bright yellow solid.

EXAMPLE 3

The t-butyl peroxy ester of fluorenone-1-carboxylic acid was also prepared from the acid in the same manner as in Example 1.

EXAMPLE 4

9-Fluorenone-4-carboxylic acid (80 gms) (Aldrich Chemical Co.) and 800 ml concentrated nitric acid were placed into a two liter 3-necked flask equipped with stirrer, condenser, heater and thermometer. The mixture was heated to 90° C. for 1½ hours. Mixture was then poured into ice water. The resulting ppt of 7-nitro-9-fluorenone-4-carboxylic acid (7-NF acid) was washed with water, dried and recrystallized from glacial acidic acid, yielding bright yellow crystals having a Mp: 264°–266° C. (uncorrected).

To a 500 ml flask equipped with stirrer, condenser and drying tube were added: 15.5 gm 7-NF acid; 12.8 gm $PCl_5$; 100 gm toluene and 5 ml DMF. The mixture was refluxed for 6 hrs. The hot liquid reaction product was then decanted and cooled after which the yellow ppt. was filtered, washed with hexane, collected and dried. The melting point of the resulting 7-NF acid chloride was 199°–201° C. (uncorrected).

The desired t-butyl perester of 7-nitro-9-fluorenone-4-carboxylic acid (7NFP) was then prepared by reaction of 10.12 gms of the 7-NF acid chloride; 4.27 gms of triethylamine; 3.49 gms t-butyl hydroperoxide; and 300 ml methylene dichloride. The reaction was conducted by adding the hydroperoxide and triethyl amine in 50 mls of the methylene dichloride dropwise with stirring to a one liter flask in an ice bath containing the remaining ingredients over 15 min. The mixture was stirred for 4 hours. 200 ml ether was then added and the ppt. filtered and discarded. The solvent was removed from the remaining solution to yield 7-NFP as a yellow solid having a MP of about 170°–175° C. (uncorrected) with decomposition.

EXAMPLE 5

A diacid, 9-fluorenone-2,7-dicarboxylic acid, and the corresponding acid chloride were prepared by the method of Sulzberg & Cotter, J. Org. Chem., 35 2762,2767(1970). The corresponding di-t-butyl perester (2,7-DFP) was then prepared using the procedures of Example 4.

Compounds of the invention are advantageously utilized in compositions with free radical curable monomers. Useful concentrations are typically within the range 0.1–10 weight percent based on monomer weight. Preferred ranges are between about 1 and 5%.

The inventive compounds can be used to initiate polymerization even when irradiated through UV filtering materials.

EXAMPLE 6

A composition comprising polyethylene glycol dimethacrylate with about 5 weight percent 4FP was prepared. A film of the material was irradiated with a medium pressure mercury lamp (Technocure System). The film cured within 5 seconds.

A 20 mil film of the same composition was then irradiated with the same lamp through a ⅜″ polycarbonate filter. The transmission spectrum of the filter showed 0% transmission of light below about 390 nm. The film cured in 10 seconds. Cure was also effected through polycarbonate headlight covers.

The inventive compounds have also been used to cure methacrylate compositions through laminated auto glass and poly(methyl methacrylate).

Compounds of the invention are stable for extended periods of time in compositions of polymerizable monomers.

EXAMPLE 7

A hydroxypropyl methacrylate capped block copolymer comprising a flexible segment of butadiene/acrylonitrile and rigid segments obtained from toluene diisocyanate and hydrogenated bisphenol A, (80 weight percent) was mixed with isobornyl methacrylate (18 weight percent) and 2 weight percent 4FP. A thin film of this mixture cured completely in 30 seconds when irradiated through polycarbonate and in 10 seconds when irradiated directly. The mixture was stored at room temperature in an opaque plastic syringe for about 2 months after which the material appeared to cure as rapidly as when fresh.

EXAMPLE 8

In order to evaluate the relative efficiency of the inventive compounds as visible and thermal initiators samples of 4FP, 2FP and 7NFP were compared to t-butyl perbenzoate (TBP) in a composition containing 60% of a methacrylate terminated polyester-urethane resin (PEUMA) and 40% hydroxypropyl methacrylate. The respective initiators were added at molar levels equivalent to 0.5% TBP by weight.

The compositions were placed on glass slides as specified in Table I and irradiated through a polycarbonate filter. Results are given in Table I.

TABLE I

| | VISIBLE LIGHT CURING | |
|---|---|---|
| Initiator | Glass Slide* | Glass Slides 0 Gap # |
| 7NFP | 20 sec - cured with tacky surface | 15 sec. cured |
| 4FP | 20 sec uncured 40 sec gelled | 30-35 sec. cured |
| 2FP | 20 sec - surface cure 50 sec cured - tacky | 25 sec. cured |
| TBP | NEG | NEG 100 sec |
| Blank | NEG | — |

*3 drops of formulation placed on glass slide
3 drops of formulation between two glass slides
Other samples of the same compositions were heat cured as indicated in Table II.

TABLE II

| | HEAT CURING | | |
|---|---|---|---|
| Initiator | Dark/Ambient (film or glass slide) | Dark 130-140° C. 10 min (between glass slides) | 130-140° C. 2 min (¼" in metal cup) |
| 7NFP | No cure | Fixtured-cured | Partial cure |
| 4FP | No cure | Fixtured-cured | Partial cure |
| TBP | No cure | Fixtured-cured | Cured |
| Blank | No cure | No cure | No cure |

EXAMPLE 9

The capability of the inventive compounds to initiate anaerobic cure was demonstrated with a formulation consisting of 4.84 wt. % 4FP, 1.08% saccharin, 300 PPM NaEDTA, 120 PPM Napthoquinone, and the balance poly(ethylene glycol) dimethacrylate. This sample was compared to two control compositions, one containing an equivalent amount of TBP (3.16%) in place of the 4FP and the other, a blank, containing no initiator. The compositions were applied between 1" sandblasted steel laps primed with Primer N™, an anaerobic activator sold by Loctite Corporation. After 20 minutes the 4FP and TBP compositions had both fixtured whereas the blank did not fixture even after 20 minutes.

EXAMPLE 10

Compositions were prepared by intimate mixing of the ingredients listed in Table III. Each composition was cured by placing three drops between glass slides and irradiating through a polycarbonate filter as in Example 8. Compositions A and C gelled in 20-25 sec. Composition B gelled within 20 secs. and cured hard within 25 secs.

TABLE III

| | Composition | | |
|---|---|---|---|
| Ingredients | A | B | C |
| PEUMA resin | 22.0 g | 22.0 g | 22.0 g |
| Hydroxypropyl methacrylate | 14.98 g | 14.98 g | 14.98 g |
| 4FP | .19 g | | |
| 2,7-DFP | | .26 | .13 |

Acrylic functional monomers and prepolymers (i.e., compounds with acrylate, methacrylate, ethacrylate, etc. functionality) are the preferred ethylenically unsaturated compounds in the curable compositions of the invention. However, other free radical polymerizable compounds may also be used in the inventive compositions. Examples of such other compounds include acrylonitrile, methacrylonitrile, acrylamide, methacrylamide, N-substituted acrylamides, vinyl propionate, vinyl succinate, vinyl ethers, styrene, alkyl styrenes, halo styrenes, divinyl benzene, vinyl napthalene, N-vinyl pyrrolidone, vinyl chloride, vinylidene chloride, diallyl phthalate, diallyl maleate, triallyl isocyanurate, triallyl phosphate and ethylene glycol diallyl ether. Prepolymers containing functional groups which will react with free radicals to crosslink or copolymerize with the foregoing monomers may also be compounded with the inventive photoinitiators to produce curable compositions.

The efficiency of the inventive compounds as visible light initiators will vary depending on the nature of the $R^1$ and $R^2$ substituents which increase the wavelength of the maximum absorbance in the UV-Vis spectrum of the acid will produce more efficient visible light photoinitiators, provided that the molecule continues to absorb sufficient energy to cleave the perester or diacyl peroxide linkage. Also, since the cleavage reaction for diacyl peroxides has a lower activation energy than for peroxy esters, the embodiments of the invention in which $R^1$ is acyl will generally be more efficient visible light initiators than those in which $R^1$ is alkyl. An example of a diacyl peroxide of the invention is the reaction product of fluorenone carboxylic acid chloride and m-chloroperbenzoic acid or its sodium or potassium salt.

I claim:

1. A peroxy compound having the general formula:

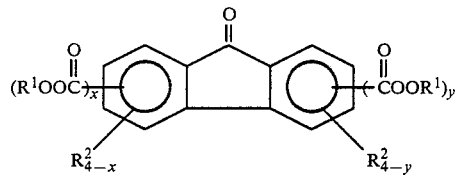

where
$R^1$ is alkyl, aralkyl, alkoxalkyl, alkenyl, alkynyl or carboxyalkyl;
$R^2$ is any group which does not cause spontaneous decomposition of the peroxy group;
x and y are integers between 0 and 4 and x+y is greater than or equal to 1.

2. A compound as in claim 1 where $R^2$ is H, alkyl, alkoxy, carboalkoxyl, silyl, nitro, alkenyl, alkynyl, halo, or when $R^1$ is not carboxyalkyl, amino, alkylamino or dialkylamino.

3. A compound as in claim 1 where x equals 1 and y equals 0.

4. A compound as in claim 1 wherein x equals 1 and y equals 1.

5. A compound as in claim 3 wherein the $R^2$ groups include at least one nitro group.

6. A compound as in claim 3 wherein the peroxy group is located in the 1,2, or 4 position.

7. A compound as in claim 1 wherein $R^1$ is t-butyl.

8. A compound as in claim 1 comprising a polymeric backbone having at least one group defined by the general formula of claim 1 attached thereto through an $R^1$ or $R^2$ group.

9. A compound as in claim 1 decomposable into free radicals upon exposure to light of greater than 400 nm wavelength.

10. A compound as in claim 1 selected from the t-butyl peroxy esters of:
 (a) fluorenone-1-carboxylic acid;
 (b) fluorenone-2-carboxylic acid;
 (c) fluorenone-4-carboxylic acid;

(d) fluorenone-2,5-dicarboxylic acid;
(e) fluorenone-2,7-dicarboxylic acid;
(f) fluorenone-2,6-dicarboxylic acid;
(g) 7-nitrofluorenone-2-carboxylic acid;
(h) 7-methoxyfluorenone-2-carboxylic acid;
(i) 7-acetylfluorenone-2-carboxylic acid;
(j) 7-chlorofluorenone-2-carboxylic acid;
(k) 7-bromofluorenone-2-carboxylic acid;
(l) 7-cyanofluorenone-2-carboxylic acid;
(m) 7-ethylfluorenone-2-carboxylic acid;
(n) 7-butylfluorenone-2-carboxylic acid;
(o) 7-butoxycarbonylfluorenone-2-carboxylic acid;
(p) 7-propoxycarbonylfluorenone-2-carboxylic acid;
(q) N,N-dialkyl-7-aminofluorenone-2-carboxylic acid;
(r) 4,5,7-trinitrofluorenone-2-carboxylic acid;
(s) 4,5-dinitrofluorenone-2,7-dicarboxylic acid;
(t) 2,5,7-trinitrofluorenone-4-carboxylic acid; and
(u) 7-nitrofluorenone-4-carboxylic acid.

11. In a free radical curable composition, a cure catalyst comprising a peroxy ester compound as defined by the general formula

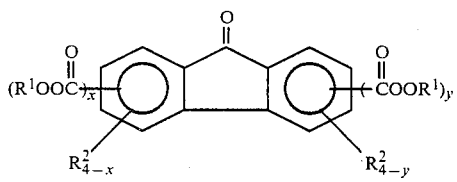

wherein
R$^1$ is alkyl, aralkyl, alkoxyalkyl, alkenyl, alkynyl or carboxyalkyl
R$^2$ is any group which does not cause spontaneous decomposition of the peroxy group;
x and y are integers between 0 and 4 and x plus y is greater than or equal to 1.

12. A composition as in claim 11 where the free radical curable composition comprises at least acrylic functional monomer or prepolymer.

13. A composition as in claim 12 further comprising an activator of the decomposition of said peroxy compound into free radicals.

14. A composition as in claim 11 wherein said peroxy ester structure is linked to a polymeric backbone through an R$^1$ or R$^2$ group.

15. A composition as in claim 11 wherein said peroxy compound decomposable into free radicals upon exposure to light of greater than 400 nm wavelength.

16. A method of preparing a visible light active photoinitiator comprising reacting an unsubstituted or substituted fluorenone carboxylic or dicarboxylic acid chloride with an organic hydroperoxide.

17. A method of providing a cured coating on a substrate having shadow areas not accessible by direct radiation, the method comprising applying a coating of a free radical curable composition to the substrate, the curable composition including:
(a) a peroxy initiator of the general formula

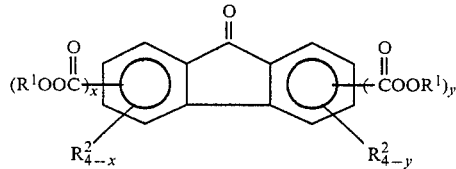

where
R$^1$ is alkyl, aralkyl, alkoxyalkyl, alkenyl, alkynyl or carboxalkyl;
R$^2$ is any group which does not cause spontaneous decomposition of the peroxy group;
x and y are integers between 0 and 4 and x plus y is greater than or equal to 1, and
(b) a peroxide activator,
exposing the substrate to UV or visible light to rapidly cure the light accessible areas and curing the light inaccessible areas by chemical activation of said peroxy initiator.

18. A method as in claim 17 wherein said light inaccessible areas are cured at ambient temperature.

19. A method of curing a free radically polymerizable formulation comprising an olefinically unsaturated compound and a compound of the formula:

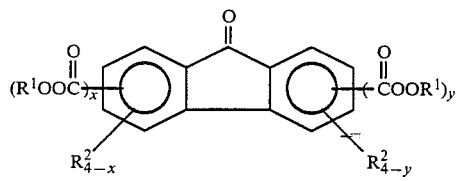

wherein
R$^1$ is alkyl, aralkyl, alkoxyalkyl, alkenyl, alkynyl, carboxyalkyl, or carboxyaryl;
R$^2$ is any group which does not cause spontaneous decomposition of the peroxy groups;
x and y are integers between 0 and 4 and x plus y is greater than or equal to 1,
the method comprising exposing the formulation to visible light for sufficient time to cure the formulation.

20. A method as in claim 19 where R$^1$ is alkyl, aralkyl, alkoxyalkyl, alkenyl, alkynyl or carboxyalkyl.

21. A method as in claim 20 where R$^1$ is alkyl.

22. A method as in claim 19 where R$^2$ includes at least one nitro group.

23. A method as in claim 21 where the unsaturated compound is an acrylic functional compound.

24. A peroxy compound as in claim 1 wherein R$^1$ is alkyl.

* * * * *